(12) United States Patent
Zigler

(10) Patent No.: US 6,733,439 B2
(45) Date of Patent: May 11, 2004

(54) CENTERING MECHANISM FOR PROBE

(75) Inventor: Arie Zigler, Washington, DC (US)

(73) Assignee: Apti Inc., Washington, DC (US)

( * ) Notice: Subject to any disclaimer, the term of this patent is extended or adjusted under 35 U.S.C. 154(b) by 0 days.

(21) Appl. No.: 09/804,487

(22) Filed: Mar. 12, 2001

(65) Prior Publication Data

US 2002/0128536 A1 Sep. 12, 2002

(51) Int. Cl.⁷ .................................................. A61B 1/04
(52) U.S. Cl. ............... 600/115; 604/96.01; 604/102.02; 606/192
(58) Field of Search .............................. 600/114, 115, 600/116; 604/96.01, 101.01, 101.02, 101.03, 102.01, 102.02, 102.03, 103, 103.03, 103.06, 103.07, 103.09; 606/192, 193, 194, 195, 196

(56) References Cited

U.S. PATENT DOCUMENTS

| | | | | |
|---|---|---|---|---|
| 4,276,874 A | * | 7/1981 | Wolvek et al. ................. 600/18 |
| 4,552,127 A | * | 11/1985 | Schiff ........................... 600/18 |
| 4,649,922 A | * | 3/1987 | Wiktor ......................... 606/194 |
| 4,664,114 A | * | 5/1987 | Ghodsian ............... 604/101.05 |
| 4,884,573 A | * | 12/1989 | Wijay et al. ................. 606/194 |
| 5,549,551 A | * | 8/1996 | Peacock et al. ......... 604/103.05 |
| 5,961,536 A | * | 10/1999 | Mickey et al. .......... 604/96.01 |
| 6,004,290 A | * | 12/1999 | Davis .................... 604/103.03 |
| 6,022,319 A | * | 2/2000 | Willard et al. ............... 600/470 |
| 6,200,307 B1 | * | 3/2001 | Kasinkas et al. ............... 606/7 |

* cited by examiner

Primary Examiner—Linda C. M. Dvorak
Assistant Examiner—Michael Peffley
(74) Attorney, Agent, or Firm—Rossi & Associates

(57) ABSTRACT

A centering mechanism accurately centers a probe as it moves through a pathway having a changing shape, diameter, and direction. More specifically, the invention provides a probe centering device that includes a ring shaped resilient balloon, a front stopper that fixes a location of a first side of the balloon, and a biasing mechanism that applies a biasing force to a second side of the balloon. The biasing mechanism includes a rear stopper, a spring and a pusher, wherein the spring is located between the rear stopper and the pusher and the pusher is in contact with the second side of the balloon. A flexible member is preferably provided to cover and protect the biasing mechanism.

7 Claims, 1 Drawing Sheet

CENTERING MECHANISM FOR PROBE

FIELD OF THE INVENTION

The invention relates in general to a probe that is inserted into a pathway within the human body such as an endoscopic or cardioscopic probe. More specifically, the invention is directed to a centering mechanism for centering a probe within a pathway such as a gastrointestinal tract, artery or other vessel.

BACKGROUND OF THE INVENTION

Endoscopic and cardioscopic diagnostic probes are known in the art. Conventional probes permit physicians to visually observe the interior surface of a patient's pathway such as a gastrointestinal track (GI), artery or other vessel. To perform certain diagnostic procedures, it is preferable that the probe be placed in the center of the pathway. However, the shape diameter and direction of pathways such as the human GI tract are constantly changing, making it difficult to maintain the probe in the proper position.

It would therefore be desirable to provide a probe with a centering mechanism which centers the probe accurately as it moves through a pathway having a changing shape, diameter, and direction.

SUMMARY OF THE INVENTION

The invention provides a centering mechanism which accurately centers a probe as it moves through a pathway having a changing shape, diameter, and direction. More specifically, the invention provides a probe centering device that includes a ring shaped resilient balloon, a front stopper that fixes a location of a first side of the balloon, and a biasing mechanism that applies a biasing force to a second side of the balloon. The biasing mechanism includes a rear stopper, a spring and a pusher, wherein the spring is located between the rear stopper and the pusher and the pusher is in contact with the second side of the balloon. A flexible member is preferably provided to cover and protect the biasing mechanism.

Other advantages and features of the invention will become apparent from the following detailed description of the preferred embodiments and the accompanying drawings.

BRIEF DESCRIPTION OF THE DRAWINGS

The invention will now be described with reference to certain preferred embodiments thereof and the accompanying drawings, wherein.

DETAILED DESCRIPTION OF THE PREFERRED EMBODIMENTS

Figure 1:
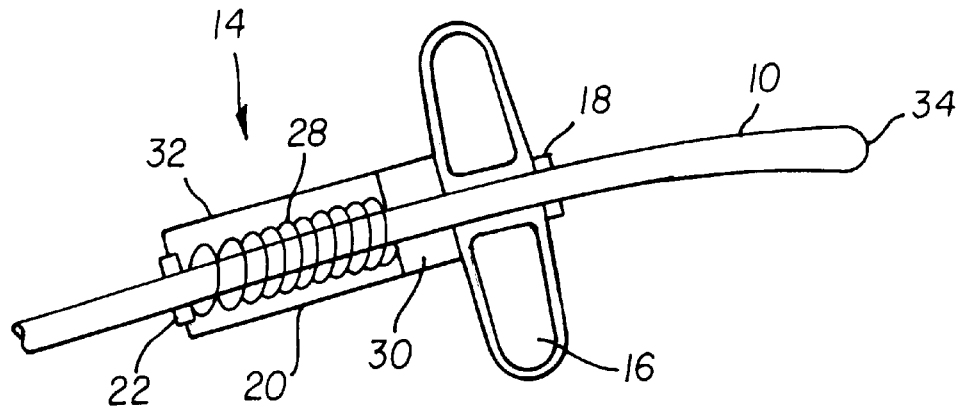
FIG. 1 is a side view of a centering mechanism in accordance with the present invention with the balloon fully expanded.

FIG. 1 illustrates a centering mechanism 14 in accordance with a preferred embodiment of the invention which is installed on a diagnostic probe 10. The centering mechanism 14 preferably includes a donut or ring shaped balloon 16, a forward stopper 18, a biasing device 20, and a rear stopper 22. The centering mechanism 14 is installed on the diagnostic probe 10 such that the donut shaped balloon 16 encircles the probe 10 near a distal end 34 thereof.

The balloon 16 is preferably a flexible bladder which is filled with silicone gel, for example, the same material utilized in implant devices. The flexible bladder may be composed of any suitable resilient bio-compatible material. The balloon 16, however, may alternatively be filled with any other suitable gel, liquid or gas. Further, a supply line can be provided so that the balloon 16 is inflated once it is placed within the pathway.

The forward stopper 18 fixes the location of one side of the balloon 16 with respect to the probe 10. The forward stopper 18 is preferably an annular clamp which fits tightly around the probe 10. The forward stopper 18 may be composed of a rubber band, a nylon clamp, or any other bio-compatible material having sufficient force to prevent the balloon 16 from moving along the length of the probe 10.

Figure 2:
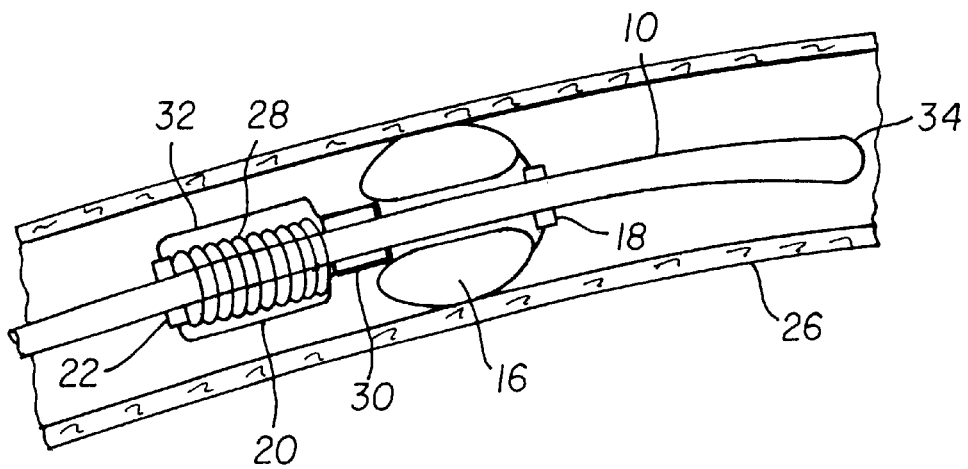
FIG. 2 is a side view of the centering mechanism of FIG. 1 located within a pathway with the balloon contracted.

The biasing device 20 is located between the rear stopper 22 and the balloon 16, such that the biasing device 20 applies a force to the balloon 16 that causes the balloon 16 to compress along the length of the probe 10 and to expand radially. The biasing device 20 preferably applies sufficient force to the balloon 16 to cause the balloon 16 to come into contact with a wall 26 of the pathway being probed as shown in FIG. 2, but does not prevent the balloon 16 from contracting once the diameter or shape of the pathway varies. Thus, the biasing device 20 allows the shape of the balloon 16 to constantly vary as the probe 10 is moved along the pathway, which thereby causes the probe 10 to remain centered within the pathway.

In the illustrated embodiment, the biasing device 20 preferably utilizes a coil spring 28 that applies a biasing force to a pusher 30 that contacts the balloon 16. One end of the coil spring 28 abuts the pusher 30 while the opposite end abuts the rear stopper 22. The rear stopper 22, like the forward stopper 18, is preferably an annular clamp which fixes one end the probe 10. The rear stopper 18 fits tightly around the probe 10, and may be composed of a rubber band, a nylon clamp, or any other bio-compatible material having a high tensile strength. The pusher 30 is preferably a cylindrical sleeve type member which fits closely around the exterior of the probe 10 and slides back and forth along the longitudinal axis of the probe 10.

A flexible membrane 32 is preferably provided to prevent material from invading the spring 28 or pusher 30. The flexible member 32 may be composed of any suitable bio-compatible material including silicone.

In operation, a physician inserts the probe 10 into a pathway of a patient, for example the GI track, an artery or other vessel. The interior shape, diameter, and direction of such pathways are constantly varying. As the probe 10 moves forward, it is automatically centered within the pathway by the balloon 16, which is normally biased by the biasing mechanism 20 for maximum expansion. In response to a decreasing interior diameter, interior walls of the pathway flatten the balloon 16 causing the pusher 30 to compress the coil spring 28 against the rear stopper 22. In response to an increased interior diameter, the coil spring 28 pushes the pusher 30 into the balloon 16 causing the diameter of the balloon 16 increase. The variation in balloon 16 expansion causes the probe 10 to remain substantially centered within the pathway.

The centering mechanism 14 may be provided as a retrofit package for installation on conventional diagnostic probes 10. Alternatively, the probe 10 can be designed to include the centering mechanism 14.

The invention has been described with reference to certain preferred embodiments thereof. It will be understood, however, that modification and variations are possible within the scope of the appended claims.

What is claimed is:

1. A device comprising:

a diagnostic probe; and a centering mechanism that centers the diagnostic probe within a pathway while the diagnostic probe performs a diagnostic operation;

wherein the centering mechanism includes a ring shaped resilient balloon, a front stopper that fixes a location of a first side of the balloon, and a biasing mechanism that applies a biasing force to a second side of the balloon; and wherein the resilient balloon is in an inflated state when the diagnostic probe performs the diagnostic operation, thereby centering the diagnostic probe within the pathway.

2. A device as claimed in claim 1; wherein the biasing mechanism includes a rear stopper, a spring and a pusher.

3. A device as claimed in claim 2, wherein the spring is located between the rear stopper and the pusher and the pusher is in contact with the second side of the balloon.

4. A device as claimed in claim 3, further comprising a flexible member that covers the biasing mechanism.

5. A device as claimed in claim 1, wherein the centering mechanism is installed on the diagnostic probe such that the ring shaped resilient balloon encircles the diagnostic probe at a distal end thereof.

6. A device as claimed in claim 1, wherein the biasing mechanism allows the shape of the balloon to constantly vary as the diagnostic probe is moved along the pathway, thereby causing the diagnostic probe to remained centered in the pathway.

7. A device as claimed in claim 1, wherein the diagnostic probe is utilized to image the pathway.

* * * * *